United States Patent
Cruse et al.

(10) Patent No.: US 8,008,524 B2
(45) Date of Patent: Aug. 30, 2011

(54) PROCESS FOR THE PREPARATION OF THIOCARBOXYLATE SILANE

(75) Inventors: Richard W. Cruse, Yorktown Height, NY (US); Tiberiu L. Simandan, Marietta, OH (US)

(73) Assignee: Momentive Performance Materials Inc., Albany, NY (US)

( * ) Notice: Subject to any disclaimer, the term of this patent is extended or adjusted under 35 U.S.C. 154(b) by 183 days.

(21) Appl. No.: 12/286,587

(22) Filed: Oct. 1, 2008

(65) Prior Publication Data

US 2009/0036701 A1    Feb. 5, 2009

Related U.S. Application Data

(62) Division of application No. 10/881,839, filed on Jun. 30, 2004.

(60) Provisional application No. 60/484,962, filed on Jul. 3, 2003.

(51) Int. Cl.
*C07C 327/00*   (2006.01)
*C07F 7/04*   (2006.01)

(52) U.S. Cl. .......................... 562/26; 556/429

(58) Field of Classification Search .............. 562/26; 556/429

See application file for complete search history.

(56) References Cited

U.S. PATENT DOCUMENTS

| | | | |
|---|---|---|---|
| 3,627,802 A | 12/1971 | Lee | |
| 3,637,789 A | 1/1972 | Pierre | |
| 5,405,985 A | 4/1995 | Parker et al. | 556/427 |
| 5,468,893 A | 11/1995 | Parker et al. | 556/427 |
| 5,583,245 A | 12/1996 | Parker et al. | 556/427 |
| 5,663,396 A | 9/1997 | Musleve et al. | 556/427 |
| 6,172,251 B1 | 1/2001 | Parker | 556/427 |
| 6,294,683 B1 | 9/2001 | Johnson et al. | 556/427 |
| 6,384,255 B1 | 5/2002 | Backer et al. | 556/427 |
| 6,384,256 B1 | 5/2002 | Backer et al. | 556/427 |
| 6,448,426 B1 | 9/2002 | Backer et al. | 556/427 |
| 6,534,668 B2 | 3/2003 | Backer et al. | 556/427 |
| 6,680,398 B1 | 1/2004 | Boswell et al. | 556/429 |
| 2005/0277781 A1 | 12/2005 | Cruse et al. | |

FOREIGN PATENT DOCUMENTS

| | | | |
|---|---|---|---|
| JP | 2003-146967 | * | 5/2003 |
| JP | 2003206274 | * | 7/2003 |
| WO | WO99/09036 | | 2/1999 |

OTHER PUBLICATIONS

Noble, Jr., et al., "Thiobenzoic Acid [Benzoic acid, thio]," Organic Syntheses, Coll. vol. 4, p. 924 (1963); vol. 32, p. 101 (1952).
"Organic Syntheses", Collective vol. 4, J. Wiley, New York, 1963, p. 924.
Block et al., "2-Thiabicyclo [2.2.1] hept-5-ene and Its S-Oxides and 3-Alkyl Derivatives: Sulfine and Sulfene Cyclopentadiene Diels-Alder Adducts. Conversion of the Cyclopentadiene-Sulfine Adducts into 2-Oxa-3-thiabicyclo [3.3.0] oct-7-enes, Novel Bicyclic Sultenes," Journal of Organic Chemistry (1987), 52, pp. 809-818, ISSN: 0022-3263.
Tacke et al., "Derivatives of β-(Trimethylsilyl) alanine with SiCH2NH2, SiCH2OH, or SiCH2SH Functionality: Synthesis of the Silicon-Containing α-Amino Acids rac- and (R)-Me2Si(CH2R)CH2CH(NH2)COOH (R=NH2, OH, SH)," Organometallics (2002), 21, pp. 2619-2626.
Tacke, et al., "(Thioacetoxy-S-methyl)diorganylsilane and (Mercaptomethyl)-diorganylsilane: Synthese und Eigenschaften," Journal of Organometallic Chemistry (1990), 388, pp. 57-62.

* cited by examiner

*Primary Examiner* — Jafar Parsa

(74) *Attorney, Agent, or Firm* — Dominick G. Vicari; Joseph S. Ostroff

(57) ABSTRACT

An aqueous process is described in which thiocarboxylate silane is produced from haloalkyl silane by reaction of the haloalkyl silane with an aqueous solution of thiocarboxylate salt. Also described is a process for the preparation of aqueous thiocarboxylate salt from a sulfide and/or hydrosulfide and an acid chloride and/or acid anhydride.

23 Claims, No Drawings

PROCESS FOR THE PREPARATION OF THIOCARBOXYLATE SILANE

CROSS REFERENCE TO RELATED APPLICATIONS

This application is a divisional application of U.S. patent application Ser. No. 10/881,839 filed Jun. 30, 2004, and claims the benefit of U.S. Provisional Application Ser. No. 60/484,962, filed Jul. 3, 2003, the entire contents of which are incorporated by reference herein.

BACKGROUND OF THE INVENTION

A large body of prior art exists in conjunction with the composition of matter, preparation, and uses of polysulfide silanes and to a lesser extent, mercaptosilanes, in rubber and other applications. In nearly all of this prior art, the methods taught for the preparation of these silanes involve solvents other than water and anhydrous conditions. In fact, it is taught that the presence of water during preparation or storage is detrimental to the stability and/or integrity of the silane compositions. The prior art describes preparation methods which require elaborate means to achieve and maintain anhydrous conditions such as the use of large quantities of hazardous metallic sodium and hydrogen sulfide.

BRIEF DESCRIPTION OF THE INVENTION

An aqueous process is described in which thiocarboxylate silane is produced from haloalkyl silane by reaction of the haloalkyl silane with an aqueous solution of a salt of a thiocarboxylic acid in the presence or absence of a phase transfer catalyst.

Also described is a novel, simple and efficient process for the preparation of the aqueous thiocarboxylate salt (also known as thioalkanoic acid salt and as thioalkanoate salt) intermediate employing readily available carboxylic acid derivatives, in particular, acid chlorides and acid anhydrides.

The present invention teaches a simple and efficient process of the manufacture of thiocarboxylate silanes from aqueous solutions of sodium sulfide or sodium hydrosulfide, carboxylic acid chlorides or anhydrides, and haloalkyl-functional alkoxysilanes. The process requires no solvent other than water, uses existing aqueous sulfide waste streams as the sulfur source, and requires no hazardous alkali metals or hydrogen sulfide as a feedstock.

DETAILED DESCRIPTION OF THE INVENTION

Thiocarboxylate Silane

The thiocarboxylate silanes, whose preparation by an aqueous route is described herein, may be represented by Formulae 1, 2, and 3:

$$(R-Y-S-)_a G^2(-SiX_3)_c \qquad (1)$$

$$G^1[-Y-S-G^2(-SiX_3)_c]_n \qquad (2)$$

$$[G^1(-Y-S-)_a]_b[G^2(-SiX_3)_c]_d \qquad (3)$$

wherein Y is carbonyl, C(=O); each occurrence of R is chosen independently from the set of groups comprising hydrogen, alkyl groups that may or may not contain unsaturation, alkenyl groups, alkynyl groups, aryl groups and aralkyl groups, with each R containing from 0 to about 30 carbon atoms; each separate occurrence of $G^1$ and $G^2$ is independently R or a polyvalent group derived by substitution of an alkyl, alkenyl, aryl or aralkyl group, wherein $G^1$ and $G^2$ can contain from 1 to about 40 carbon atoms, with the proviso that $G^1$ and $G^2$ are not hydrogen; each separate occurrence of $G^1$ is independently R or a polyvalent group derived by substitution of an alkyl, alkenyl, aryl or aralkyl group, wherein $G^1$ can contain from 1 to about 40 carbon atoms; each separate occurrence of $G^2$ is independently a polyvalent (divalent or higher-valent) group derived by substitution of an alkyl, alkenyl, aryl or aralkyl group, wherein $G^1$ and $G^2$ can contain from 1 to about 40 carbon atoms; each occurrence of X is independently a member selected from the group consisting of RO—, $R_2C$=NO—, $R_2NO$—, or $R_2N$—, —R, and —$(OSiR_2)_t(OSiR_3)$, wherein each R is as above; at least one X is not —R and each occurrence of the subscript t is an integer from 0 to about 50; each occurrence of the subscript a is independently an integer from 1 to about 6; each occurrence of the subscript b is independently an integer from 1 to about 100; each occurrence of the subscript c is independently an integer from 1 to 6; and, each occurrence of the subscript d is independently an integer from 1 to about 100.

As used herein, alkyl includes straight, branched and cyclic alkyl groups; alkenyl includes any straight, branched, or cyclic alkenyl group containing one or more carbon-carbon double bonds, where the point of substitution can be either at a carbon-carbon double bond or elsewhere in the group; and alkynyl includes any straight, branched, or cyclic alkynyl group containing one or more carbon-carbon triple bonds and optionally also one or more carbon-carbon double bonds as well, where the point of substitution can be either at a carbon-carbon triple bond, a carbon-carbon double bond, or elsewhere in the group. Specific examples of alkyls include methyl, ethyl, propyl and isobutyl. Specific examples of alkenyls include vinyl, propenyl, allyl, methallyl, ethylidenyl norbornane, ethylidene norbornyl, ethylidenyl norbornene and ethylidene norbornenyl. Specific examples of alkynyls include acetylenyl, propargyl and methylacetylenyl.

As used herein, aryl includes any aromatic hydrocarbon from which one hydrogen atom has been removed; aralkyl includes any of the aforementioned alkyl groups in which one or more hydrogen atoms have been substituted by the same number of like and/or different aryl (as defined herein) substituents; and arenyl includes any of the aforementioned aryl groups in which one or more hydrogen atoms have been substituted by the same number of like and/or different alkyl (as defined herein) substituents. Specific examples of aryls include phenyl and naphthalenyl. Specific examples of aralkyls include benzyl and phenethyl. Specific examples of arenyls include tolyl and xylyl.

As used herein, cyclic alkyl, cyclic alkenyl, and cyclic alkynyl also include bicyclic, tricyclic, and higher cyclic structures as well as the aforementioned cyclic structures further substituted with alkyl, alkenyl, and/or alkynyl groups. Representative examples include norbornyl, norbornenyl, ethylnorbornyl, ethylnorbornenyl, ethylcyclohexyl, ethylcyclohexenyl, cyclohexylcyclohexyl and cyclododecatrienyl.

The key functional group (—YS—) present in the silanes of the present invention is the thiocarboxylate ester group, —C(=O)S— (any silane with this functional group is a "thiocarboxylate ester silane"). The silanes of the present invention include those wherein Y is $R^0C$(=O)— representing a simple subset of the structures represented by Formulae 1-2.

Preferred structures within the set wherein Y is equal to $R^0C$(=O)— are those wherein $R^0$ has a primary carbon attached to the carbonyl and is preferably a $C_2$-$C_{20}$ straight- or branched-chain alkyl, more preferably a $C_6$-$C_{18}$ straight-chain alkyl. Most preferable are $C_6$-$C_{14}$ straight-chain alkyls.

Representative examples of G include monovalent hydrocarbon groups such as those described above for R; phenylene; —$(CH_2)_v$— wherein v is 1 to about 20, which represent the terminal straight-chain alkyls further substituted terminally at the other end such as —$CH_2$—, —$CH_2CH_2$—, —$CH_2CH_2CH_2$—, and —$CH_2CH_2CH_2CH_2CH_2CH_2CH_2CH_2$— and their beta-substituted analogs such as —$CH_2(CH_2)_mCH(CH_3)$— where m is 0 to about 17;—$CH_2CH_2C(CH_3)_2CH_2$—; the structure derivable from methallyl chloride, —$CH_2CH(CH_3)CH_2$—; any of the structures derivable from divinylbenzene such as —$CH_2CH_2(C_6H_4)CH_2CH_2$— and —$CH_2CH_2(C_6H_4)CH(CH_3)$— where the notation $C_6H_4$ denotes a disubstituted benzene ring; any of the structures derivable from dipropenylbenzene such as —$CH_2CH(CH_3)(C_6H_4)CH(CH_3)CH_2$— where the notation $C_6H_4$ denotes a disubstituted benzene ring; any of the structures derivable from butadiene such as —$CH_2CH_2CH_2CH_2$—, —$CH_2CH_2CH(CH_3)$— and —$CH_2CH(CH_2CH_3)$—; any of the structures derivable from piperylene such as —$CH_2CH_2CH_2CH(CH_3)$—, —$CH_2CH_2CH(CH_2CH_3)$— and —$CH_2CH(CH_2CH_3)$—; any of the structures derivable from isoprene such as —$CH_2CH(CH_3)CH_2CH_2$—, —$CH_2CH(CH_3)CH(CH_3)$—, —$CH_2C(CH_3)(CH_2CH_3)$—, —$CH_2CH_2CH(CH_3)CH_2$—, —$CH_2CH_2C(CH_3)_2$— and —$CH_2CH[CH(CH_3)_2]$—; any of the isomers of —$CH_2CH_2$-norbornyl-, —$CH_2CH_2$-cyclohexyl-; any of the diradicals obtainable from norbornane, cyclohexane, cyclopentane, tetrahydrodicyclopentadiene or cyclododecene by loss of two hydrogen atoms; the structures derivable from limonene, —$CH_2CH(4$-methyl-1-$C_6H_9$—$)CH_3$, where the notation $C_6H_9$ denotes isomers of the trisubstituted cyclohexane ring lacking substitution in the 2 position; any of the monovinyl-containing structures derivable from trivinylcyclohexane such as —$CH_2CH_2(vinylC_6H_9)CH_2CH_2$— and —$CH_2CH_2(vinylC_6H_9)CH(CH_3)$— where the notation $C_6H_9$ denotes any isomer of the trisubstituted cyclohexane ring; any of the monounsaturated structures derivable from myrcene containing a trisubstituted C=C such as —$CH_2CH[CH_2CH_2CH=C(CH_3)_2]CH_2CH_2$—, —$CH_2CH[CH_2CH_2CH=C(CH_3)_2]CH(CH_3)$—, —$CH_2C[CH_2CH_2CH=C(CH_3)_2](CH_2CH_3)$—, —$CH_2CH_2CH[CH_2CH_2CH=C(CH_3)_2]CH_2$—, —$CH_2CH_2(C=)(CH_3)[CH_2CH_2CH=C(CH_3)_2]$— and —$CH_2CH[CH(CH_3)[CH_2CH_2CH=C(CH_3)_2]]$—; and, any of the monounsaturated structures derivable from myrcene lacking a trisubstituted C=C such as —$CH_2CH(CH=CH_2)CH_2CH_2CH_2C(CH_3)_2$—, —$CH_2CH(CH=CH_2)CH_2CH_2CH[CH(CH_3)_2]$—, —$CH_2C(=CH—CH_3)CH_2CH_2CH_2C(CH_3)_2$—, —$CH_2C(=CH—CH_3)CH_2CH_2CH[CH(CH_3)_2]$—, —$CH_2CH_2C(=CH_2)CH_2CH_2CH_2C(CH_3)_2$—, —$CH_2CH_2C(=CH_2)CH_2CH_2CH[CH(CH_3)_2]$—, —$CH_2CH=C(CH_3)_2CH_2CH_2CH_2C(CH_3)_2$— and —$CH_2CH=C(CH_3)_2CH_2CH_2CH[CH(CH_3)_2]$. The preferred structures for $G^1$, $G^2$ and $G^3$ are —$CH_2$—, —$CH_2CH_2$—, —$CH_2CH_2CH_2$—, —$CH_2CH(CH_3)CH_2$— and any of the diradicals obtained by 2,4 or 2,5 disubstitution of the norbornane-derived structures listed above. The structure —$CH_2CH_2CH_2$— is more preferred.

Representative examples of R groups are branched and straight-chain alkyls of 1 to about 30 carbon atoms or more such as methyl, ethyl, propyl, isopropyl and butyl; phenyl; benzyl; tolyl; and, allyl. Preferable R groups are $C_1$ to $C_4$ alkyls and H.

Representative examples of X are methoxy, ethoxy, isobutoxy, propoxy, isopropoxy and oximato. Methoxy and ethoxy are preferred. Ethoxy is most preferred.

Preferred embodiments are wherein p is 0 to 2; X is RO—; R is hydrogen, methyl, ethyl, propyl, butyl or isopropyl; and, G is a substituted phenyl or substituted $C_2$ to $C_{20}$ straight-chain alkyl. The preferred embodiments also include structures of the form $X_3SiGSC(=O)GC(=O)SGSiX_3$ wherein G is a divalent hydrocarbon. The more preferred embodiments include those wherein p is 0, X is ethoxy and G is a $C_6$-$C_{14}$ straight-chain alkyl.

Representative examples of the silanes whose preparation is described in the present invention include 2-triethoxysilyl-1-ethyl thioacetate; 2-trimethoxysilyl-1-ethyl thioacetate; 2-(methyldimethoxysilyl)-1-ethyl thioacetate; 3-trimethoxysilyl-1-propyl thioacetate; triethoxysilylmethyl thioacetate; trimethoxysilylmethyl thioacetate; triisopropoxysilylmethyl thioacetate; methyldiethoxysilylmethyl thioacetate; methyldimethoxysilylmethyl thioacetate; methyldiisopropoxysilylmethyl thioacetate; dimethylethoxysilylmethyl thioacetate; dimethylmethoxysilylmethyl thioacetate; dimethylisopropoxysilylmethyl thioacetate; 2-triisopropoxysilyl-1-ethyl thioacetate; 2-(methyldiethoxysilyl)-1-ethyl thioacetate; 2-(methyldiisopropoxysilyl)-1-ethyl thioacetate; 2-(dimethylethoxysilyl)-1-ethyl thioacetate; 2-(dimethylmethoxysilyl)-1-ethyl thioacetate; 2-(dimethylisopropoxysilyl)-1-ethyl thioacetate; 3-triethoxysilyl-1-propyl thioacetate; 3-triisopropoxysilyl-1-propyl thioacetate; 3-methyldiethoxysilyl-1-propyl thioacetate; 3-methyldimethoxysilyl-1-propyl thioacetate; 3-methyldiisopropoxysilyl-1-propyl thioacetate; 1-(2-triethoxysilyl-1-ethyl)-4-thioacetylcyclohexane; 1-(2-triethoxysilyl-1-ethyl)-3-thioacetylcyclohexane; 2-triethoxysilyl-5-thioacetylnorbornene; 2-triethoxysilyl-4-thioacetylnorbornene; 2-(2-triethoxysilyl-1-ethyl)-5-thioacetylnorbornene; 2-(2-triethoxysilyl-1-ethyl)-4-thioacetylnorbornene; 1-(1-oxo-2-thia-5-triethoxysilylpenyl)benzoic acid; 6-triethoxysilyl-1-hexyl thioacetate; 1-triethoxysilyl-5-hexyl thioacetate; 8-triethoxysilyl-1-octyl thioacetate; 1-triethoxysilyl-7-octyl thioacetate; 6-triethoxysilyl-1-hexyl thioacetate; 1-triethoxysilyl-5-octyl thioacetate; 8-trimethoxysilyl-1-octyl thioacetate; 1-trimethoxysilyl-7-octyl thioacetate; 10-triethoxysilyl-1-decyl thioacetate; 1-triethoxysilyl-9-decyl thioacetate; 1-triethoxysilyl-2-butyl thioacetate; 1-triethoxysilyl-3-butyl thioacetate; 1-triethoxysilyl-3-methyl-2-butyl thioacetate; 1-triethoxysilyl-3-methyl-3-butyl thioacetate; 3-trimethoxysilyl-1-propyl thiooctanoate, also known as 3-trimethoxysilyl-1-propyl thioloctoate and 3-trimethoxysilyl-1-propyl thiocaprylate; 3-triethoxysilyl-1-propyl thiopalmitate; 3-triethoxysilyl-1-propyl thiooctanoate, also known as 3-triethoxysilyl-1-propyl thioloctanoate, 3-triethoxysilyl-1-propyl thiooctoate, 3-triethoxysilyl-1-propyl thioloctoate and 3-triethoxysilyl-1-propyl thiocaprylate; 3-triethoxysilyl-1-propyl thiodecanoate; 3-triethoxysilyl-1-propyl thiododecanoate, also known as 3-triethoxysilyl-1-propyl thiolaurate; 3-triethoxysilyl-1-propyl thiotetradecanoate, also known as 3-triethoxysilyl-1-propyl thiomyristate; 3-triethoxysilyl-1-propyl thiobenzoate; 3-triethoxysilyl-1-propyl thio-2-ethylhexanoate; 3-triethoxysilyl-1-propyl thio-2-methylheptanoate; bis-(3-triethoxysilyl-1-propyl) dithiophthalate; bis-(3-triethoxysilyl-1-propyl) dithio-iso-phthalate; bis-(3-triethoxysilyl-1-propyl) dithio-tere-phthalate; bis-(3-triethoxysilyl-1-propyl) dithiosuccinate; bis-(3-triethoxysilyl-1-propyl) dithiooxalate; bis-(3-triethoxysilyl-1-propyl) dithiosebacate; and, bis-(3-triethoxysilyl-1-propyl) dithioadipate.

The thiocarboxylate silane compositions included herein may be prepared as various mixtures of individual thiocarboxylate silane components, optionally including other species as well, including wherein synthetic methods result in a distribution of various silanes and including wherein mixtures of the starting components are employed for the purpose of generating mixtures of thiocarboxylate silane products. Moreover, it is understood that the partial hydrolyzates and/or condensates of these thiocarboxylate silanes (i.e., thiocarboxylate siloxanes and/or silanols) may also be encompassed by the thiocarboxylate silanes herein, in that these partial hydrolyzates and/or condensates will be a side product of most methods of manufacture of the thiocarboxylate silanes or can occur upon storage of the thiocarboxylate silanes, especially in humid conditions, or under conditions in which residual water remaining from their preparation is not completely removed subsequent to their preparation.

The inventive procedure described herein for the preparation of thiocarboxylate-functional silane involves the reaction between an aqueous solution of a salt of a thiocarboxylic acid (an aqueous solution of a thiocarboxylate salt which, therefore, contains the thiocarboxylate anion) with a haloalkyl silane in the presence or absence of a phase transfer catalyst. Optionally, mixtures of aqueous thiocarboxylate salts and/or haloalkyl silanes can be used in which case mixtures of thiocarboxylate silanes will be obtained.

As used herein, the expression "haloalkyl silane" refers to any silane whose structure can be represented by Formula 3. Thus, the expression "haloalkyl silane" as used herein includes silanes with one or more halogen substitutions for hydrogen on their hydrocarbon groups as well as other substitutions which would represent potential leaving groups during nucleophilic substitution reactions, as described below. Structures for the thiocarboxylate salts are given in Formula 4.

Structures for the haloalkyl silanes are given in Formula 5.

wherein each occurrence of $G^1$ and $G^2$ is independently R or a polyvalent group derived by substitution of an alkyl, alkenyl, aryl or aralkyl group, wherein $G^1$ and $G^2$ can contain from 1 to about 40 carbon atoms, with the proviso that $G^1$ and $G^2$ are not hydrogen, and where $G^1$ and/or $G^2$ is R, each occurrence of R is chosen independently from the set of groups comprising hydrogen, alkyl groups that may or may not contain unsaturation, alkenyl groups, alkynyl groups, aryl groups, and aralkyl groups, with each R containing from 0 to about 30 carbon atoms; Y is carbonyl, C(=O); each occurrence of M is an alkali metal; ammonium; or a mono-, di-, or tri- substituted ammonium; each occurrence of L is a halogen atom (i.e., F, Cl, Br, or I), sulfonate group, sulfinate group, or carboxylate group; each occurrence of X is independently a member selected from the group consisting of RO—, $R_2C=NO—$, $R_2NO—$ or $R_2N—$, —R, and —(OSiR$_2$)$_t$ (OSiR$_3$), wherein each R is as previously defined; at least one X is not —R and each occurrence of the subscript t is an integer of from 0 to about 50; each occurrence of the subscript a is independently an integer from 1 to about 6; each occurrence of the subscript b is independently an integer from 1 to about 100; each occurrence of the subscript c is independently an integer from 1 to about 6; each occurrence of the subscript d is independently an integer from 1 to about 100; and, each occurrence of the subscript f is independently an integer from 1 to about 6, with the proviso that ab=df.

M is an alkali metal; ammonium; or a mono-, di- or tri-substituted ammonium. Thus, M is typically a monocation, meaning it occurs as a cation, typically with a single positive charge. Dicationic ions could also be used in cases where their thiocarboxylate salts are available and are sufficiently soluble in water. As such, M is the counterion to the anionic thiocarboxylate, $[(ROC(=O)-)_p(G)_j]-Y—S^-$. Representative examples of M are sodium, potassium, ammonium, methyl ammonium and triethyl ammonium. Sodium, potassium and ammonium are preferred. Sodium is most preferred.

L is a halogen atom (i.e., F, Cl, Br, or I), sulfonate group, sulfinate group or carboxylate group. From a synthetic chemical standpoint, L is any group which can function as a leaving group during nucleophilic substitution reactions. Representative examples of L are chloride, bromide, sulfonate. L can also be a divalent group such as sulfate or phosphate. L is preferably chloro (Cl) or bromo (Br). Chloro (Cl) is most preferred.

Some preferred haloalkyl silane reactants for use herein are 3-chloromethyl-1-triethoxysilane, 3-chloroethyl-1-triethoxysilane, 3-chloropropyl-1-triethoxysilane and 3-chlorobutyl-1-triethoxysilane. Of these, 3-chloropropyl-1-triethoxysilane is more preferred.

The chemical equation(s) for reaction(s) between the aqueous thiocarboxylate salt(s) and the haloalkyl silane(s) to yield the thiocarboxylate silane(s) is(are) represented by Equations A, B, and C.

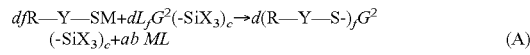

(A)

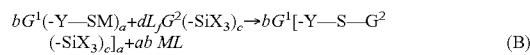

(B)

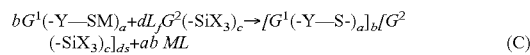

(C)

The preparation of the thiocarboxylate silane in accordance with the invention is carried out by addition of the haloalkyl silane to an aqueous solution of the thiocarboxylate salt preferably accompanied by agitation of the mixture, e.g., stirring, until the reaction has reached the desired level of completeness. Additional salt(s) may optionally be present or be added to the aqueous thiocarboxylate salt to increase the ionic strength of the reaction medium so as to further stabilize the product silane(s) against hydrolysis. Examples of such additional salts include alkali metal salts such as the sodium and potassium halides and the corresponding carbonates and nitrates. These and similar salts can be present in the reaction medium at a level of up to about 50, and preferably up to about 20 weight percent of the amount of thiocarboxylate salt reactant present therein.

The level of completeness of the reaction may be monitored by any means which distinguishes the reactants from the products, such as, for example, gas chromatography (GC), liquid chromatography (LC or HPLC), nuclear magnetic resonance spectroscopy (NMR), or infrared spectroscopy (IR) of the organic phase, or wet chemical analysis of the aqueous phase. A phase transfer catalyst may be added in one or several doses and/or in a continuous manner to the thiocarboxylate salt, the haloalkyl silane, and/or the reaction mixture before, during, and/or after the addition of the haloalkyl silane to the aqueous thiocarboxylate salt, to accelerate the reaction.

Suitable reaction conditions include temperatures of from about —30° C. to about 300° C. and pressures of ambient to about 100 atmospheres or vacuum from ambient to about 0.01 torr. Preferred conditions are from about —10° C. to about 100° C. at ambient pressure. Preferred reaction temperatures can range from about 25° C. to about 95° C. and more preferably from about 40° C. to about 85° C. Variable temperatures within the aforementioned ranges may be employed, as, for example, a gradual upward or downward ramping of the temperature during the course of the reaction.

Ordinarily, and by way of reducing the amount of siloxane-type by-product(s) that may be formed during the thiocarboxylate silane-forming reaction, it is preferred to conduct this reaction under continuous agitation, e.g., that provided by the motion of a conventional rotary stirrer. The vigorousness of the agitation will ordinarily be such as to keep the amount of siloxane-type by-product(s) produced during the thiocarboxylate silane-forming reaction to within reasonable bounds, e.g., less than about 20 weight percent, more commonly less than about 12 weight percent, and typically to within about 5 to about 10 weight percent, of the total amount of reaction product. The amount of agitation required to achieve this can be determined in a specific case by routine experimentation.

Suitable concentrations of the starting aqueous thiocarboxylate salt are from about 1 weight percent up to saturation, which can be as high as about 50 weight percent or more. Preferred concentrations are from about 20 to about 45 weight percent and more preferred, from about 30 to about 40 weight percent. Optionally, an excess of the thiocarboxylate salt relative to that demanded by the reaction stoichiometry may be used to drive the reaction to completion so as to obtain a product of minimal residual haloalkyl silane starting material, to obtain the product with minimal reaction time and/or temperature, and/or to obtain a product with minimal loss to or contamination by silane hydrolysis/condensation products. Alternatively, an excess of the haloalkyl silane relative to that demanded by the reaction stoichiometry may be used to reduce the residual aqueous thiocarboxylate salt content at the completion of the reaction to a minimum.

The reaction may be run neat (i.e., without solvent) or in the presence of solvents which are insoluble or have limited solubility in water. Examples of appropriate solvents are ethers, for example, diethyl ether; hydrocarbons, for example, hexane, petroleum ether, toluene, and xylene; and ketones, for example, methyl ethyl ketone. Toluene or xylene are preferred. Most preferred is to run the reaction in the absence of solvent (neat).

Upon completion of the reaction, the agitation is ceased resulting in the segregation of the reaction mixture into two liquid phases. The organic phase (typically the upper phase) contains the thiocarboxylate silane product and the aqueous phase contains the coproduced salts plus any salts initially present or subsequently added to increase the ionic strength of the reaction medium. If a starting aqueous solution of sufficient concentration is used, a solid phase may also separate comprised of precipitated or crystallized salts. These salts may optionally be dissolved by addition of water so as to obtain a mixture made up of mainly or exclusively of two liquid phases. These phases can then be separated by decantation. Any solvents used during the process may then be removed by distillation or evaporation. Residual water may be removed by vacuum and/or heat stripping. Residual particulates may subsequently or concurrently be removed by filtration. Residual haloalkyl silane may be removed by stripping under vacuum at elevated temperature.

Aqueous Solution of Thiocarboxylate Salt

If an aqueous solution of the thiocarboxylate salt(s) required for the preparation of the thiocarboxylate silane composition is not available, it may be prepared in a separate step preceding its use in the preparation of the thiocarboxylate silane. Alternatively, the aqueous thiocarboxylate salt may be prepared in situ and used directly thereafter, as described above, to prepare the thiocarboxylate silane composition.

If the thiocarboxylate salt is available, the aqueous solution thereof can simply be prepared by dissolving the appropriate amount of the salt into the appropriate amount of water to provide a solution of the desired concentration, or it can be prepared by dilution or evaporative concentration of whatever solution is available. Alternatively, the desired thiocarboxylate salt or aqueous solution thereof can be prepared from another salt of the desired thiocarboxylic acid. It the thiocarboxylic acid is available, the thiocarboxylate salt or aqueous solution thereof can be prepared simply by neutralizing the acid with a suitable base.

However, if neither the desired thiocarboxylic acid or one of its salts is available, it can be prepared by synthesis of the thiocarbonyl group by reaction of the appropriate acid halide and/or acid anhydride (e.g., the acid chloride) with an aqueous solution of a sulfide, a hydrosulfide, or mixture thereof (e.g., aqueous sodium hydrosulfide, NaSH), to yield an aqueous solution of the thiocarboxylate salt. If an aqueous mixture of thiocarboxylate salts is desired, the component thiocarboxylate salts can be blended, or the appropriate mixture of acid halides and/or acid anhydrides can be used in the preparation of the thiocarboxylate salts. Mixtures of one or more acid halides and acid anhydrides can optionally be used, as can mixtures of different sulfides and/or hydrosulfides when preparing either single-component or mixtures of aqueous thiocarboxylate salts.

Structures for the sulfides, hydrosulfides, and acid halides and acid anhydrides are represented by Formulae 6, 7, and 8, respectively.

$$M_2S \qquad (6)$$

$$MSH \qquad (7)$$

$$G^1(\text{-Y-L})_a \qquad (8)$$

wherein each occurrence of M is an alkali metal; ammonium; or a mono-, di-, or tri- substituted ammonium; each occurrence of L is a halogen atom (i.e., F, Cl, Br, or I), sulfonate group, sulfinate group, or carboxylate group; Y is carbonyl, $C(=O)$; each occurrence of R is chosen independently from the set of groups comprising hydrogen, alkyl groups that may or may not contain unsaturation, alkenyl groups, alkynyl groups, aryl groups and aralkyl groups with each R containing from 0 to about 30 carbon atoms; each separate occurrence of $G^1$ and $G^2$ is independently R or a polyvalent group derived by substitution of an alkyl, alkenyl, aryl or aralkyl group, wherein $G^1$ and $G^2$ can contain from 1 to 40 carbon atoms, with the proviso that $G^1$ and $G^2$ are not hydrogen; each occurrence of X is independently a member selected from the group consisting of RO—, $R_2C=NO$—, $R_2NO$— or $R_2N$—, —R, and —$(OSiR_2)_t(OSiR_3)$, wherein each R is as above; at least one X is not —R and each occurrence of the subscript t is an integer of from 0 to about 50; each occurrence of the subscript a is independently an integer from 1 to about 6; each occurrence of the subscript b is independently an integer from 1 to about 100; each occurrence of the subscript c is independently an integer from 1 to about 6; each occurrence of the subscript d is independently an integer from 1 to about 100; and each occurrence of the subscript f is independently an integer from 1 to about 6, with the proviso that ab=df.

M is an alkali metal; ammonium; or a mono-, di-, or tri-substituted ammonium. Thus, M is typically a monocation, meaning it occurs as a cation, typically with a single positive charge. Dicationic ions could also be used in cases where their sulfides or hydrosulfides are available, suitably stable, and are sufficiently solubile in water. As such, M is the counterion to the anionic sulfide or hydrosulfide anion. Representative examples of M are sodium, potassium, ammonium, methyl ammonium, and triethyl ammonium. Sodium, potassium, and ammonium are preferred. Sodium is most preferred.

L is a halogen atom (i.e., F, Cl, Br, or I), sulfonate group, sulfinate group, or carboxylate group. Representative examples of L are chloride, bromide, and any carboxylate, such as acetate, octanoate, decanoate, and dodecanoate. L could even be a divalent group, such as sulfate or phosphate. Preferred L are chloride (Cl), and carboxylate. Chloride (Cl) is most preferred. In the case where L is chloride, the reagent is an acid chloride. Where L is carboxylate, the reagent is an acid anhydride.

In the descriptions which follow, of the procedures for the preparation of aqueous thiocarboxylate salt solutions, it is to be understood, herein, that 1) The term acid halide shall refer to the acid fluoride, acid chloride, acid bromide, acid iodide, acid anhydride, or mixed acid anhydride with another carboxylic acid, other organic acid, or an inorganic acid; or any mixture thereof;
2) The term sulfide shall refer to an alkali metal, ammonium, or substituted ammonium sulfide salt; or any mixture thereof; and
3) The term, thiocarboxylate salt, shall refer to a single-component or mixture of salts of one or more than one thiocarboxylate and/or counterion (cation)

Chemical equations for reactions between the aqueous sulfides and/or hydrosulfides and the acid halides and/or acid anhydrides to yield the aqueous thiocarboxylate salts are illustrated by Equations D, E, F, and G.

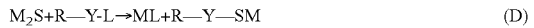

$$M_2S + R—Y-L \rightarrow ML + R—Y—SM \quad (D)$$

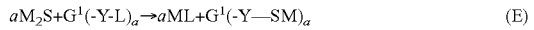

$$aM_2S + G^1(-Y-L)_a \rightarrow aML + G^1(-Y—SM)_a \quad (E)$$

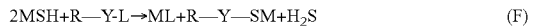

$$2MSH + R—Y-L \rightarrow ML + R—Y—SM + H_2S \quad (F)$$

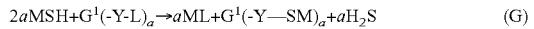

$$2aMSH + G^1(-Y-L)_a \rightarrow aML + G^1(-Y—SM)_a + aH_2S \quad (G)$$

The preparation of the aqueous thiocarboxylate salt is carried out by addition of the acid halide and/or acid anhydride to an aqueous solution of the sulfide and/or hydrosulfide and agitating the mixture. Due to the corrosive properties of the acid halide and/or acid anhydride, practical considerations suggest that this reaction be carried out in glass or in a glass-lined reactor.

A phase transfer catalyst such as any of those described infra may be added in one or several doses and/or in a continuous manner to the aqueous sulfide/hydrosulfide solution, the acid halide/acid anhydride, and/or the reaction mixture before, during, and/or after the addition of the acid halide/acid anhydride to the aqueous sulfide/hydrosulfide solution to accelerate the reaction.

Appropriate reaction conditions for the thiocarboxylate salt-forming reaction include temperatures of from about 10° C. to about 40° C., and preferably from about 20° C. to about 25° C., for batch operation and from about 20° C. to about 50° C., and preferably from about 25° C. to about 40° C., for continuous operation in order to minimize or suppress by-product formation.

Since the thiocarboxylate salt-forming reaction is fast and exothermic, in order the maintain the reaction within the aforesaid temperature conditions, it is advantageous to employ a reactor having temperature control capability, e.g., a jacket or coil through which a coolant such as chilled water or brine is circulated at an adjustable rate. In the absence of such temperature control capability, one can maintain the desired reaction temperature by controlling the rate of addition of the acid chloride reactant to the mixture of aqueous sulfide/hydrosulfide and phase transfer catalyst.

Additional conditions of the process for making the thiocarboxylate salt include a pressure of from about 0.01 torr to about 100 atmospheres, preferably from about 100 torr to about 2 atmospheres, and a molar ratio of sulfide/hydrosulfide to acid chloride/acid anhydride of from about 2:1 to about 3:1, and preferably from about 2:1 to about 2.2:1. The process is advantageously carried out with agitation of the reaction medium, e.g., employing a rotary stirrer, to minimize the formation of undesirable by-product(s). In generally, and when employing a rotary stirrer to provide agitation, the tip speed of the stirrer should be at least about 25 inches per second, preferably at least about 30 inches per second, and more preferably at least about 35 inches per second.

Concentrations of the starting aqueous sulfide/hydrosulfide can vary from about 1 weight percent up to saturation which can be as high as about 60 weight percent or more. Preferred concentrations are from about 10 to about 40 weight percent and more preferred are concentrations of from about 15 to about 25 weight percent. The reaction is usually complete when the acid halide/acid anhydride has dissolved in the aqueous phase, an exotherm is no longer evident from this reaction and the evolution of any hydrogen sulfide subsides. As previously stated, one or more additional salts may optionally be present or be added to the aqueous thiocarboxylate salt product to increase its ionic strength when used in the thiocarboxylate silane-forming reaction. At the completion of the thiocarboxylate salt-forming reaction, the solution may optionally be filtered to remove any particulate impurities and/or crystallized coproduced salts that may be present.

Aqueous Sulfide and/or Hydrosulfide

Aqueous solutions of sulfide and/or hydrosulfide for preparing the aqueous solution of thiocarboxylate salt can be obtained by dissolving the appropriate quantity of sulfide or hydrosulfide, or the appropriate quantity of each if a mixture is desired, into the appropriate quantity of water to obtain the desired concentration of sulfide and/or hydrosulfide. Alternatively, these solutions can be prepared by addition of hydrogen sulfide to an aqueous solution of the appropriate base. A ratio of one or more moles of hydrogen sulfide to one equivalent of base would yield the hydrosulfide, whereas a ratio of one mole of hydrogen sulfide to two equivalents of base would yield the sulfide. Ratios of one mole of hydrogen sulfide to between one and two equivalents of base would yield the corresponding mixtures of the hydrosulfide and sulfide. Alternatively, an aqueous solution of sulfide can also be prepared by addition of one equivalent of base to one equivalent of aqueous hydrosulfide, and an aqueous solution of hydrosulfide can also be prepared by addition of one or more equivalents of hydrogen sulfide to one equivalent of aqueous sulfide. For example, aqueous sodium hydrosulfide could be prepared by addition of one mole or an excess of hydrogen sulfide to an aqueous solution containing one mole of sodium hydroxide or sodium sulfide, and aqueous sodium sulfide could be prepared by addition of one mole of hydrogen sulfide or two moles of sodium hydrosulfide to an aqueous solution containing two moles of sodium hydroxide.

Phase Transfer Catalyst

The phase transfer catalysts used herein accelerate the preparation of the thiocarboxylate salt reactant and/or thiocarboxylate silane product by facilitating chemical reactions across the phase boundary of two immiscible liquids. The phase transfer catalysts can comprise any substance capable of facilitating transfer of reacting species, whether molecules or ions, across the phase boundary. Useful catalysts often comprise organic cations, which are capable of transferring sulfur anions such as sulfide, hydrosulfide, and thiocarboxylate from the aqueous phase into the organic phase, where these anions can then react with species in the organic phase, such as acid halides and haloalkyl silanes. The organic cations can be added as salts, or as concentrated or dilute solutions in water and/or other suitable solvents, such as alcohols. A wide variety of anions can be associated with the organic cations, such as fluoride, chloride, bromide, iodide, sulfate, bisulfate, carbonate, bicarbonate, hydroxide, phosphate, carboxylate, thiocarboxylate, etc. Additionally useful as phase transfer catalysts are crown ethers, cryptands, polyethylene glycols, heterogenized catalysts (bound to polymeric substrates), and the like.

A preferred group of phase transfer catalysts, ammonium and phosphonium salts, whose use is described herein is represented by Formula 7:

$$(R^1R^2R^3R^4Q^+)_nA^{-n} \quad (9)$$

wherein each separate occurrence of $R^1$, $R^2$, $R^3$, and $R^4$ is independently one of the members listed above for R; Q is nitrogen or phosphorous; $A^{-n}$ is a monovalent or polyvalent anion where the minus sign denotes that the species is an anion, and n denotes the number of negative charges on the anion; and, the subscript n is a positive integer of from 1 to about 6. In general, the more hydrophilic and more structurally symmetrical phase transfer catalyst species are preferred.

Representative examples of $R^1$, $R^2$, $R^3$, and $R^4$ are branched and straight-chain alkyls, such as methyl, ethyl, propyl, isopropyl, butyl, isobutyl, hexyl, octyl, decyl, dodecyl, tetradecyl, octadecyl, phenyl, benzyl, tolyl, cyclohexyl, methylcyclohexyl and allyl. Methyl, ethyl, butyl, and octyl are preferred.

Representative examples of $A^{-n}$ are fluoride, chloride, bromide, iodide, sulfate, bisulfate, carbonate, bicarbonate, hydroxide, phosphate, carboxylate, thiocarboxylate, sulfide and hydrosulfide. Chloride, bromide and hydroxide are preferred. Chloride is most preferred.

Representative examples of suitable phase transfer catalysts are tetramethylammonium chloride, tetramethylammonium bromide, tetramethylammonium iodide, tetramethylammonium hydroxide, tetraethylammonium chloride, tetraethylammonium bromide, tetraethylammonium iodide, tetraethylammonium hydroxide, tetrabutylammonium chloride, tetrabutylammonium bromide, tetrabutylammonium iodide, tetrabutylammonium hydroxide, methyltributylammonium chloride, methyltributylammonium bromide, methyltributylammonium iodide, methyltributylammonium hydroxide, tetraoctylammonium chloride, tetraoctylammonium bromide, tetraoctylammonium iodide, tetraoctylammonium hydroxide, methyltrioctylammonium chloride, methyltrioctylammonium bromide, methyltrioctylammonium iodide, methyltrioctylammonium hydroxide, benzyltrimethylammonium chloride, benzyltrimethylammonium bromide, benzyltriethylammonium chloride, benzyltributylammonium chloride, dibenzyldimethylammonium chloride, dibenzyldimethylammonium bromide, dibenzyldiethylammonium chloride, dibenzyldibutylammonium chloride, tetrabutylphosphonium bromide, tetrabutylphosphonium chloride, trioctyl (octadecyl) phosphonium iodide, tributyl (tetradecyl) phosphonium chloride and aqueous solutions thereof The preferred phase transfer catalysts are aqueous solutions of tetraethylammonium chloride, tetrabutylammonium chloride, tetrabutylammonium bromide, tetrabutylammonium hydroxide, methyltributylammonium chloride, tetraoctylammonium chloride, tetraoctylammonium bromide, methyltrioctylammonium chloride, methyltrioctylammonium bromide, methyltrioctylammonium iodide, methyltrioctylammonium hydroxide, benzyltrimethylammonium chloride, benzyltriethylammonium chloride, benzyltributylammonium chloride, dibenzyldiethylammonium chloride, dibenzyldibutylammonium chloride, tetrabutylphosphonium bromide and tetrabutyl phosphonium chloride. Aqueous solutions of tetraethylammonium chloride, tetrabutylammonium chloride, tetrabutylammonium bromide, tetrabutylammonium hydroxide, methyltributylammonium chloride, tetraoctylammonium chloride, methyltrioctylammonium chloride, methyltrioctylammonium bromide, methyltrioctylammonium hydroxide, benzyltriethylammonium chloride, benzyltributylammonium chloride, dibenzyldibutylammonium chloride, tetrabutylphosphonium bromide and tetrabutylphosphonium chloride are more preferred.

The phase transfer catalyst can be added at any point during the reaction, either all at once, in two or more doses, or in a continuous or semi-continuous manner, or as any combination thereof. A single phase transfer catalyst may be used, or a combination of several, added as a blend, as individual components, or any combination thereof. Different catalysts may optionally be added at different points along the entire reaction sequence. The phase transfer catalyst(s) may be added only to the first step, in which aqueous sulfide and/or hydrosulfide is reacted with the acid halide; or only to the second step, in which the aqueous thiocarboxylate is reacted with the haloalkyl silane. Alternatively, the phase transfer catalyst(s) may be added to both steps in the same or different levels.

The quantity of phase transfer catalyst to be used depends on the desired rate of reaction and level of side products which can be tolerated, among other factors. The reactions can be run without a phase transfer catalyst. However, if a phase transfer catalyst is used, appropriate concentrations to be used during the reactions are from a concentration of about 1 ppm (part per million, by weight) to about 3 percent by weight. Preferred concentrations are from about 10 ppm to about 1 weight percent. The most preferred concentrations are from about 50 ppm to about 0.5 weight percent. Quantities below about 1 ppm of phase transfer catalyst can also be used but this will give results similar to that obtained without the use of a phase transfer catalyst.

Of the examples which follow, Examples 1-4 are illustrative (a) of the process of making aqueous thiocarboxylate salt reactant and (b) the process of making thiocarboxylate silane product in accordance with the invention and Examples 5-8 are illustrative of making aqueous thiocarboxylate salt reactant (with Example 8 being that of a continuous process) that can be used to prepare thiocarboxylate silane in accordance with the invention.

EXAMPLE 1

A. Preparation of Aqueous Sodium Thiooctanoate

A 12.9 weight percent aqueous solution of sodium sulfide was prepared by dissolving sodium sulfide (144 grams, 1.84 moles) in the form of hydrated flakes (240 grams, 60%) into 880 grams of water in a 5-liter round-bottomed flask. A dropping funnel was charged with octanoyl chloride (300 grams, 1.84 moles). The temperature of the sodium sulfide solution in the 5-liter flask measured 21° C. The addition of the octanoyl chloride was begun with stirring of the contents of the 5-liter flask with a mechanical stirrer, and immediately, 0.15 grams of a concentrated aqueous solution of methyltrioctylammonium chloride was added to the 5-liter flask. The addition of the octanoyl chloride was completed within 5-10 minutes with external cooling of the 5-liter flask. The contents of the 5-liter flask reached a maximum temperature of 68° C. The contents of the 5-liter flask were then cooled to ambient temperature and stirring was stopped, yielding a clear, slightly viscous, one-phase aqueous solution of sodium thiooctanoate (also known as sodium thioloctanoate and as sodium thiocarprylate) and sodium chloride.

B. Preparation of 3-Octanoylthio-1-propyltriethoxysilane

The aqueous solution of sodium thiooctanoate was heated to 50° C. and stirred with a mechanical stirrer throughout this procedure. To this solution was added 3-chloro-1-propyltriethoxysilane (444 grams, 1.84 moles) all at once. Immediately thereafter was added 0.15 grams of a concentrated aqueous solution of methyltrioctylammonium chloride. A temperature of 50° C. was maintained for 9 hours, with continued stirring, whereupon the temperature was raised to and subsequently maintained at 74° C. for an additional 15 hours, with continuous stirring. At this point, the solution was allowed to cool to ambient temperature, the stirring was stopped, and the organic phase separated from the aqueous phase by decantation in a separatory funnel. Gas chromatography and mass spectrometry (GC and GCMS) revealed a product containing 80% 3-octanoylthio-1-propyltriethoxysilane and 15.5% residual 3-chloro-1-propyltriethoxysilane (reported purities are based on area percent GC responses). The product was vacuum stripped at 110° C. at 0.1 torr to remove volatiles, primarily 3-chloro-1-propyltriethoxysilane, to yield a product of 94% purity. Product identity using this process confirmed by nuclear magnetic resonance spectroscopy (NMR).

EXAMPLE 2

A. Preparation of Aqueous Sodium Thiooctanoate

A 16 weight percent aqueous solution of sodium sulfide was prepared by dissolving sodium sulfide (101 grams, 1.29 moles) in the form of hydrated flakes (168 grams, 60%) into 463 grams of water in a 5-liter round-bottomed flask. A dropping funnel was charged with octanoyl chloride (210.5 grams, 1.294 moles). The temperature of the sodium sulfide solution in the 5-liter flask measured 23° C. The addition of the octanoyl chloride to the 5-liter flask was begun with stirring of the contents of the 5-liter flask with a mechanical stirrer, immediately after the addition of 0.21 grams of a concentrated aqueous solution of methyltrioctylammonium chloride to the 5-liter flask. The addition of the octanoyl chloride was completed in 3 minutes with external cooling of the 5-liter flask using an ice-water bath. The contents of the 5-liter flask reached a maximum temperature of 59° C. The contents of the 5-liter flask were then cooled to ambient temperature and stirring was stopped, yielding a clear, slightly viscous, one-phase aqueous solution of sodium thiooctanoate and sodium chloride.

B. Preparation of 3-Octanoylthio-1-propyltriethoxysilane

The aqueous solution of sodium thiooctanoate was heated to 50° C. and stirred with a mechanical stirrer throughout this procedure. To this solution was added, all at once, 0.21 grams of a concentrated aqueous solution of methyltrioctylammonium chloride. Immediately thereafter was added a solution of 3-chloro-1-propyltriethoxysilane (310 grams, 1.29 moles) in 23.6 grams of n-tetradecane. Over the next 15-20 minutes, the temperature of the contents of the 5-liter flask was increased to 55° C., with continued stirring. This temperature was then maintained for 5-6 hours, with continued stirring. The temperature was then ramped up to 70° C. over the next 7 minutes, and maintained for about another 2 hours, with continued stirring, whereupon the temperature was raised to and subsequently maintained at 78° C. for an additional 24 hours or so, with continuous stirring. After cooling to ambient temperature, the organic phase was separated from the aqueous phase. Gas chromatography and mass spectrometry (GC and GCMS) revealed a product containing 85% 3-octanoylthio-1-propyltriethoxysilane and 5.5% residual 3-chloro-1-propyltriethoxysilane (reported purities are based on area percent GC responses). Vacuum stripping at 110° C. at 0.1 torr to remove volatiles, primarily 3-chloro-1-propyltriethoxysilane, yielded a product of 90+% purity. Product identity using this process confirmed by nuclear magnetic resonance spectroscopy (NMR).

EXAMPLE 3

A. Preparation of Aqueous Sodium Thiooctanoate

A 16 weight percent aqueous solution of sodium sulfide was prepared by dissolving sodium sulfide (101 grams, 1.29 moles) in the form of hydrated flakes (168 grams, 60%) into 463 grams of water in a 5-liter round-bottomed flask. This solution was then converted to an aqueous solution of sodium hydrosulfide (NaSH) by saturating it with an excess of hydrogen sulfide by adding hydrogen sulfide with stirring until no more was absorbed. A dropping funnel was charged with octanoyl chloride (210.5 grams, 1.294 moles). The temperature of the sodium hydrosulfide solution in the 5-liter flask measured 23° C. The addition of the octanoyl chloride to the 5-liter flask was begun with stirring of the contents of the 5-liter flask with a mechanical stirrer, immediately after the addition of 0.21 grams of a concentrated aqueous solution of methyltrioctylammonium chloride to the 5-liter flask. Hydrogen sulfide was liberated during the addition of the octanoyl chloride. The addition of the octanoyl chloride was completed in 3 minutes with external cooling of the 5-liter flask using an ice-water bath. The contents of the 5-liter flask reached a maximum temperature of 59° C. The contents of the 5-liter flask were then cooled to ambient temperature and stirring was stopped, yielding a clear, slightly viscous, one-phase aqueous solution of sodium thiooctanoate and sodium chloride.

B. Preparation of 3-Octanoylthio-1-propyltriethoxysilane

The aqueous solution of sodium thiooctanoate was heated to 50° C. and stirred with a mechanical stirrer throughout this procedure. To this solution was added, all at once, 0.21 grams of a concentrated aqueous solution of methyltrioctylammonium chloride. Immediately thereafter was added a solution of 3-chloro-1-propyltriethoxysilane (310 grams, 1.29 moles) in 23.6 grams of n-tetradecane. Over the next 15-20 minutes, the temperature of the contents of the 5-liter flask was increased to 55° C., with continued stirring. This temperature was then maintained for 5-6 hours, with continued stirring. The temperature was then ramped up to 70° C. over the next 7 minutes, and maintained for about another 2 hours, with continued stirring, whereupon the temperature was raised to and subsequently maintained at 78° C. for an additional 24 hours or so, with continuous stirring. After cooling to ambient temperature, the organic phase was separated from the aqueous phase. Gas chromatography and mass spectrometry (GC and GCMS) revealed a product containing 85% 3-octanoylthio-1-propyltriethoxysilane and 5.5% residual 3-chloro-1-propyltriethoxysilane (reported purities are based on area percent GC responses). Vacuum stripping at 110° C.

at 0.1 torr to remove volatiles, primarily 3-chloro-1-propyl-triethoxysilane, yielded a product of 90+% purity. Product identity using this process confirmed by nuclear magnetic resonance spectroscopy (NMR).

EXAMPLE 4

A. Preparation of Aqueous Sodium Thiooctanoate

A 20 weight percent aqueous solution of sodium sulfide was prepared by dissolving sodium sulfide (39 grams, 0.5 moles) in the form of hydrated flakes (65 grams, 60%) into 130 grams of water in a 1-liter round-bottomed flask. This solution was then converted to an aqueous solution of sodium hydrosulfide (NaSH) by saturating it with an excess of hydrogen sulfide by adding hydrogen sulfide with stirring until no more was absorbed. A dropping funnel was charged with octanoyl chloride (81.3 grams, 0.5 moles). The temperature of the sodium hydrosulfide solution in the 1-liter flask measured 29.7° C. The addition of the octanoyl chloride to the 1-liter flask was begun with stirring of the contents of the 1-liter flask with a mechanical stirrer, immediately after the addition of 1 gram of a concentrated aqueous solution of methyltrioctylammonium chloride to the 1-liter flask. Hydrogen sulfide was liberated during the addition of the octanoyl chloride. After the completion of the addition of the octanoyl chloride, the contents of the 1-liter flask were cooled to ambient temperature and stirring was stopped, yielding a clear, slightly viscous, one-phase aqueous solution of sodium thiooctanoate and sodium chloride.

B. Preparation of 3-Octanoylthio-1-propyltriethoxysilane

The aqueous solution of sodium thiooctanoate was heated to 80° C. and stirred with a mechanical stirrer throughout this procedure. To this solution was added, all at once, 4 grams of a concentrated aqueous solution of tetrabutylammonium bromide. Immediately thereafter was added a solution of 3-chloro-1-propyltriethoxysilane (120 grams, 0.5 moles). This mixture was kept at 80° C. with continued stirring for 6 hours, and then allowed to cool to ambient temperature. After cooling to ambient temperature, the organic phase was separated from the aqueous phase. Gas chromatography and mass spectrometry (GC and GCMS) revealed a product containing 93% 3-octanoylthio-1-propyltriethoxysilane. Product identity using this process confirmed by nuclear magnetic resonance spectroscopy (NMR).

EXAMPLE 5

Preparation of Sodium Thiodecanoate

Into a 5-liter round-bottomed flask was added 204.0 grams of sodium sulfide and 410.0 grams of water and the mixture was stirred at room temperature until the solids were dissolved. A total of 53.5 grams of hydrogen sulfide was added below the surface until bubbling was seen in the trap about 75 minutes after the hydrogen sulfide addition was begun. The reaction mixture was then cooled with an ice water bath to 16° C. Decanoyl chloride was then added slowly. Foaming was observed after about half of the decanoyl chloride had been added. At this point, the addition of decanoyl chloride was slowed and occasionally stopped to control foaming. The reactor temperature was kept at about 17° C. The decanoyl chloride addition was complete after a total of 4 hours. The pH of the resulting solution containing sodium thiodecanoate was measured with pH paper, and gave a reading of 11. An additional 10.0 grams of decanoyl chloride was then titrated into the solution to neutralize it, giving a final neutral pH reading.

EXAMPLE 6

Preparation of Sodium Thiodecanoate

Into a 2-liter round-bottomed flask was added 82 grams of sodium sulfide and 164 grams of water and the mixture was stirred at room temperature until the solids were dissolved. An excess of hydrogen sulfide was added below the surface until bubbling was seen in the trap. The reaction mixture was then cooled with an ice water bath to 17° C. Decanoyl chloride was then added slowly. Foaming was observed after about half of the decanoyl chloride had been added. At this point, the addition of decanoyl chloride was slowed and occasionally stopped to control foaming. The reactor temperature was kept at about 17° C. The decanoyl chloride addition was complete after a total of 2.5 hours. The pH of the resulting solution containing sodium thiodecanoate was measured with pH paper, giving an alkaline reading. An additional 2.7 grams of decanoyl chloride was then titrated into the solution to neutralize it, giving a final neutral pH reading.

EXAMPLE 7

Preparation of Sodium 2-ethylhexanoate

Into a 1-liter round-bottomed flask was added 78 grams of sodium sulfide and 210 grams of water and the mixture was stirred at room temperature until the solids were dissolved. A total of 18.5 grams of hydrogen sulfide was then added below the surface until bubbling was seen in the trap. The reaction mixture was then cooled to 25° C. At this point, a total of 92 grams of 2-ethylhexanoyl chloride was added slowly, with a concomitant temperature rise to about 45° C. No foaming was observed. The pH of the resulting solution containing sodium 2-ethylhexanoate was measured with pH paper, and gave a reading of 11. An additional 9.5 grams of 2-ethylhexanoyl chloride was then titrated into the solution to neutralize it, giving a final neutral pH reading.

EXAMPLE 8

Continuous Process for the Preparation of Sodium Thiooctanoate

Into a 1-liter jacketed flask, 25 weight percent aqueous sodium hydrosulfide (NaSH) solution and octanoyl-chloride were charged via rate-controlled diaphragm pumps. The temperature was maintained at about 25° C. by recirculation of cold water through the jacket. The reactor-retained product was approximately 425 grams. The product was continuously taken off using a diaphragm pump. The feed rates of the reactants were:

| | |
|---|---|
| 25 weight percent aqueous sodium hydrosulfide solution | 2.43 cc/minute |
| octanoyl chloride | 0.83 cc/minute |

The foregoing feed rates provided a residence time of about 2 hours and a molar ratio of NaSH to octanoyl chloride of 2.2:1. The tetrabutylammonium bromide phase transfer catalyst was prepared as a 50 weight percent aqueous solution and was added to the reaction medium via the NaSH feed at a 1200 ppm level. At steady state, samples were taken for GC analysis. Sodium thiooctanoate was produced with an average 98.5% purity.

EXAMPLES 9-14

Effect of Rotary Stirrer Tip Speed on Yield of Sodium Thiooctanoate Produced by Continuous Process In these examples, the effect of various rotary stirrer tip speeds on the production of sodium thiooctanoate product and undesirable sodium octanoate by-product was evaluated in connection with a continuous process. As in the case of the continuous process described in Example 8, the reactions of Examples 9 to 14 were carried out in a 1-liter cc jacketed flask with the reactants, i.e., aqueous sodium hydrosulfide (NaSH) containing 600 ppm tertiarybutylammonium bromide (TBAB) based on the weight of octanoyl chloride (OC), and a molar ratio of NaSH to OC of approximately 2.2:1, being introduced to the flask via rate-controlled diaphragm pumps. The other conditions of the thiocarboxylate salt-forming reaction of each example and the results thereof are set forth in the table below.

| Example | NaSH, Wt. % Aqueous | Total Time of Continuous Reaction, min | Total Wt. of Reaction Products, Gm | NaSH Feed Rate, cc/min |
|---|---|---|---|---|
| 9 | 40 | 365 | 1321 | 2.9 |
| 10 | 45 | 367 | 1258.4 | 3.0 |
| 11 | 45 | 368 | 1183.2 | 2.8 |
| 12 | 45 | 234 | 878.88 | 2.1 |
| 13 | 45 | 367 | 1314.9 | 3.1 |
| 14 | 45 | 259 | 909.3 | 2.1 |

| Example | OC Feed Rate, cc/min | Reactor Temp. °C. | Sodium Octanoate, Wt. % | Sodium Thiooctanoate, Wt. % | Sodium Thiooctanoate, % of Total Reaction Product | Stirrer Speed, rpm | Stirrer Tip Speed, in/sec. |
|---|---|---|---|---|---|---|---|
| 9 | 0.80 | 30-32 | 5.63 | 14.09 | 71.45 | 150 | 20.4* |
| 10 | 0.83 | 30-32 | 5.85 | 15.42 | 72.50 | 175 | 23.8 |
| 11 | 0.84 | 30-32 | 3.26 | 20.11 | 86.05 | 200 | 27.2 |
| 12 | 0.84 | 30-32 | 1.11 | 22.54 | 95.31 | 225 | 30.6 |
| 13 | 0.8 | 30-32 | 0.62 | 21.49 | 97.20 | 250 | 34 |
| 14 | 0.83 | 30-32 | 0.56 | 20.89 | 97.39 | 300 | 40.8 |

*Formation of gel observed.

As these data show, with increased tip speed, the amount of desired sodium thiooctanoate product as a percentage of the total reaction product increases and at a tip speed of at least about 30 in/sec. and greater, the purity of the reaction product (95.31% sodium thiooctanoate) is such as to provide a desirably high level of purity of thiocarboxylate silane when directly used for the production thereof. It may be noted that the desired stirrer tip speeds disclosed herein apply to all rotary stirrers regardless of their size. Thus, as stirrer size increases to accommodate reactors of larger diameter, the lower will be its r.p.m. to achieve a desired tip speed.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A process for the preparation of an aqueous solution of a salt of a thiocarboxylic acid which comprises reacting an aqueous solution of a sulfide and/or hydrosulfide with an acid halide and/or acid anhydride in the presence of a phase transfer catalyst to provide the aqueous solution of thiocarboxylic acid salt, wherein the structures of the sulfide, hydrosulfide, acid halide and acid anhydride are represented by the formulae:

$$M_2S \quad (6)$$

$$MSH \quad (7)$$

$$G^1(-Y-L)_a \quad (8)$$

wherein
each occurrence of M is an alkali metal; ammonium; or a mono-, di-, or tri-substituted ammonium;
each occurrence of L is a halogen atom, sulfonate group, sulfinate group, or carboxylate group; Y is carbonyl, C(=O);
each occurrence of R is chosen independently from the set of groups comprising hydrogen, alkyl groups, alkenyl groups, alkynyl groups, aryl groups and aralkyl groups with each R containing from 0 to about 30 carbon atoms;
each occurrence of $G^1$ is independently R or a polyvalent group derived from an alkyl, alkenyl, aryl or aralkyl group, containing from 1 to about 40 carbon atoms,
each occurrence of the subscript a is independently an integer from 1 to 6 and wherein the phase transfer catalyst is represented by the formula:

$$(R^1R^2R^3R^4Q^+)_nA^{-n} \quad (9)$$

wherein
each separate occurrence of $R^1$, $R^2$, $R^3$ and $R^4$, is, independently, an R, wherein R is a hydrogen, an alkyl, an alkenyl, an alkynyl, an aryl or an aralkyl containing from 0 to about 30 carbon atoms; Q is nitrogen or phosphorus; and $A^{-n}$ is a monovalent or polyvalent anion where the minus sign denotes that the species is an anion, and n denotes the number of negative charges on the anion; and, wherein the subscript n is a positive integer of from 1 to about 6.

2. The process of claim 1 wherein M is selected from the group consisting of sodium, potassium, ammonium, methyl ammonium and triethyl ammonium.

3. The process of claim 1 wherein L is selected from the group consisting of chloride, bromide, sulfonate, sulfate, phosphate or carboxylate.

4. The process of claim 1 wherein $R^1$, $R^2$, $R^3$ and $R^4$ are, independently, selected form the group consisting of straight and branched chain alkyls.

5. The process of claim 4 wherein $R^1$, $R^2$, $R^3$ and $R^4$ are, independently, selected from the group consisting of methyl, ethyl, propyl, isopropyl, butyl, isobutyl, hexyl, octyl, decyl, dodecyl, tetradecyl, octadecyl, phenyl, benzyl, tolyl, cyclohexyl, methylcyclohexyl and allyl.

6. The process of claim 4 wherein $A^{-n}$ is selected from the group consisting of fluoride, chloride, bromide, iodide, sulfate, bisulfate, carbonate, bicarbonate, hydroxide, phosphate, carboxylate, thiocarboxylate, sulfide and hydrosulfide.

7. The process of claim 5 wherein $A^{-n}$ is selected from the group consisting of fluoride, chloride, bromide, iodide, sulfate, bisulfate, carbonate, bicarbonate, hydroxide, phosphate, carboxylate, thiocarboxylate, sulfide and hydrosulfide.

8. The process of claim 1 wherein the phase transfer catalyst is selected from the group consisting of tetramethylammonium chloride, tetramethylammonium bromide, tetramethylammonium iodide, tetramethylammonium hydroxide, tetraethylammonium chloride, tetraethylammonium bromide, tetraethylammonium iodide, tetraethylammonium hydroxide, tetrabutylammonium chloride, tetrabutylammonium bromide, tetrabutylammonium iodide, tetrabutylammonium hydroxide, methyltributylammonium chloride, methyltributylammonium bromide, methyltributylammonium iodide, methyltributylammonium hydroxide, tetraoctylammonium chloride, tetraoctylammonium bromide, tetraoctylammonium iodide, tetraoctylammonium hydroxide, methyltrioctylammonium chloride, methyltrioctylammonium bromide, methyltrioctylammonium iodide, methyltrioctylammonium hydroxide, benzyltrimethylammonium chloride, benzyltrimethylammonium bromide, benzyltriethylammonium chloride, benzyltributylammonium chloride, dibenzyldimethylammonium chloride, dibenzyldimethylammonium bromide, dibenzyldiethylammonium chloride, dibenzyldibutylammonium chloride, tetrabutylphosphonium bromide, tetrabutylphosphonium chloride, trioctyl (octadecyl) phosphonium iodide, tributyl (tetradecyl) phosphonium chloride, combinations thereof and aqueous solutions thereof.

9. The process of claim 1 carried out in a batch operation at from about 10° C. to about 40° C. and from about 20° C. to about 50° C. in a continuous operation.

10. The process of claim 1 carried out in batch operation at from about 20° C. to about 25° C. and in continuous operation at from about 25° C. to about 40° C.

11. The process of claim 1 wherein the molar ratio of sulfide and/or hydrosulfide to acid chloride and/or acid anhydride is from about 2:1 to about 3:1.

12. The process of claim 1 wherein the molar ratio of sulfide and/or hydrosulfide to acid chloride and/or acid anhydride is from about 2:1 to about 2.2:1.

13. The process of claim 1 wherein the concentration of sulfide and/or hydrosulfide in the aqueous solution thereof ranges from about 10 to about 40 weight percent.

14. The process of claim 1 wherein the concentration of sulfide and/or hydrosulfide in the aqueous solution thereof ranges from about 15 to about 25 weight percent.

15. The process of claim 1 which comprises reacting alkali metal hydrosulfide with alkanoyl halide in the presence of phase transfer catalyst and under agitation to provide an aqueous solution of alkali metal thiolalkanoate containing phase transfer catalyst.

16. The process of claim 1 conducted under agitation of sufficient vigor as to provide product thiocarboxylic acid salt of at least about 95 weight percent purity based on the total weight of all the reaction products.

17. The process of claim 16 wherein agitation is provided by a rotary stirrer operating at a tip speed of at least about 30 in/sec.

18. The process of claim 9 conducted under agitation of sufficient vigor as to provide product thiocarboxylic acid salt of at least about 95 weight percent purity based on the total weight of all the reaction products.

19. The process of claim 18 wherein agitation is provided by a rotary stirrer operating at a tip speed of at least about 30 in/sec.

20. The process of claim 15 wherein the reaction temperature is maintained within the range of from about 10° C. to about 40° C. for a batch operation and from about 20° C. to about 50° C. for a continuous operation and agitation is such as to provide thiocarboxylic acid salt of at least about 95 weight percent purity based on the total weight of all the reaction products.

21. The process of claim 20 wherein the alkali metal hydrosulfide is sodium hydrosulfide, the alkanoyl halide is octanoyl chloride, the phase transfer catalyst is tetrabutylammonium bromide and the salt of thiocarboxylic acid is sodium thiooctanoate.

22. The process of claim 20 wherein the salt of thiocarboxylic acid in aqueous solution and containing phase transfer catalyst is reacted with haloalkyl silane to provide thiocarboxylate silane.

23. The process of claim 21 wherein the sodium thiooctanoate in aqueous solution and containing tetrabutylammonium bromide phase transfer agent is reacted with 3-chloro-1-propytriethoxysilane to provide 3-octanoylthio-1-propytriethoxysilane.

* * * * *